United States Patent [19]

Levine et al.

[11] Patent Number: 5,667,098
[45] Date of Patent: Sep. 16, 1997

[54] APPARATUS AND METHOD FOR REMOVING, DILUTING AND DISPENSING FLUID FROM A FLEXIBLE TUBE

[75] Inventors: Marshall S. Levine; Daniel S. Levine; David E. Levine, all of Wayne, Pa.

[73] Assignee: Alpha Scientific Corporaton, Malvern, Pa.

[21] Appl. No.: 395,903

[22] Filed: Feb. 28, 1995

[51] Int. Cl.⁶ .................................................. B67D 7/00
[52] U.S. Cl. ........................... 222/1; 222/88; 222/206; 222/215; 222/420; 222/83.5
[58] Field of Search .............................. 141/18, 21, 329, 141/330; 222/1, 81, 83.5, 88, 206, 212, 215, 420

[56] References Cited

U.S. PATENT DOCUMENTS

| | | |
|---|---|---|
| 887,919 | 5/1908 | Carpenter . |
| 983,348 | 2/1911 | Carpenter . |
| 1,152,601 | 9/1915 | Carpenter . |
| 1,152,602 | 9/1915 | Carpenter . |
| 1,364,889 | 1/1921 | Rupp ................................ 222/83.5 X |
| 1,680,616 | 8/1928 | Horst ................................ 141/330 |
| 2,083,479 | 6/1937 | Speare .............................. 222/88 X |
| 2,260,875 | 10/1941 | Vranichar ........................ 222/83.5 X |
| 2,311,367 | 2/1943 | Chambers . |
| 2,431,192 | 11/1947 | Munson . |
| 2,784,882 | 3/1957 | Du Bois ........................... 222/215 |
| 3,059,643 | 10/1962 | Barton . |
| 3,366,278 | 1/1968 | Fobes . |
| 3,809,290 | 5/1974 | Schmit ............................. 222/88 |
| 4,244,467 | 1/1981 | Cavazza . |
| 4,491,244 | 1/1985 | Yanes ............................... 222/88 |
| 4,600,125 | 7/1986 | Maynard, Jr. .................... 222/88 X |
| 5,071,034 | 12/1991 | Corbiere . |
| 5,114,033 | 5/1992 | Golias . |
| 5,224,619 | 7/1993 | Dilworth et al. ................ 222/88 X |
| 5,310,085 | 5/1994 | Lontrade et al. ................ 220/420 X |
| 5,551,606 | 9/1996 | Rai et al. ......................... 141/330 X |
| 5,558,257 | 9/1996 | Braun .............................. 222/215 X |

FOREIGN PATENT DOCUMENTS

| | | |
|---|---|---|
| 0249533 | 12/1987 | European Pat. Off. . |
| 0489977 | 6/1992 | European Pat. Off. . |

OTHER PUBLICATIONS

Advertisement of Porex Scientific, "Keep A Lid On It", CTP System — one page 1993.

*Primary Examiner*—Andres Kashnikow
*Assistant Examiner*—Kenneth Bomberg
*Attorney, Agent, or Firm*—William H. Eilberg

[57] ABSTRACT

A device for removing fluid from a flexible tube includes a container having an opening and a sharp cannula located inside the container. The cannula is positioned to puncture the flexible tube when it is inserted through the opening, so that fluid in the tube flows through the cannula and collects at the bottom of the container. A diluent may be added to the container through the same opening. The cannula is affixed to the wall of the container by passing the cannula through a dimple formed in that wall. A spout formed in the container allows fluid to be dispensed from the container. When dispensing fluid from the container, the opening is preferably sealed with a finger, and the size of the spout determines the rate at which fluid flows out of the spout.

35 Claims, 5 Drawing Sheets

APPARATUS AND METHOD FOR REMOVING, DILUTING AND DISPENSING FLUID FROM A FLEXIBLE TUBE

BACKGROUND OF THE INVENTION

1. Field of the Invention

This invention relates to the field of blood banking, wherein blood is stored in tubular segments which are then pierced to obtain blood specimens for screening. This invention provides a fast and safe method of piercing which reduces the risk that technicians will come into contact with hazardous specimens. The invention also provides means for containing, diluting, mixing and dispensing the specimen.

2. State of the Prior Art

In blood banks throughout the world, specimens are routinely screened to match the donor blood with the recipient's blood. The typical way of obtaining specimens is to acquire a small quantity of the blood from the plastic tube that originally transferred blood from the donor to the blood storage bag.

After the donor has given blood, the tube connecting the donor's arm with the storage bag is partitioned into a plurality of segments, by pinching and heat sealing the tube at several locations along its length. The pinching and sealing is done while the tube is still filled with blood, and while it is still attached to the blood storage bag. Thus, the contents of the tube will be guaranteed to be the same as the contents of the bag. The segmented tube has the appearance of a series of sausage links, each link containing an identical blood specimen. Due to the heat sealing, the segments of the tube comprise separate and independent compartments of blood. It is useful to have a plurality of such independent blood-filled segments so that one can perform different tests, on the same blood, at different times. Each segment can be removed from the others by cutting it off along the heat-sealed portion, without disturbing the contents of any segment.

The present invention is concerned with the process of removing blood from one of the segments. When tests for typing or cross-matching are performed, one or more segments are torn off the chain at the pinched locations. Over time, gravity separates the blood cells from the serum. Alternatively, one can speed the separation process by centrifugation. The end of the segmented tube containing the liquid cells is cut, usually with a scissors. A few drops of the blood cells are then squeezed from one end of the segment into a test tube, diluted with saline and then transferred to other containers for analyses.

The above-described practice is hazardous because the technician often comes into contact with blood and can become infected with viruses such as HIV and hepatitis, especially if the contaminated scissors accidentally cuts the technician. Also the scissors must be cleaned between uses to avoid contamination, a practice which is time consuming and requires the consumption of cleaning preparations.

A device currently in use avoids these hazards by means of a sharp puncturing prong which is positioned inside a test tube so that the segment becomes pierced when it comes in contact with the prong. The prong is not rigidly attached to the tube, but is only suspended from the edge of the tube. The prong of this device often fails to contact the segment, and therefore fails to puncture the segment, because it is not maintained in the proper position. Furthermore, the prong is known to impede the passage of the blood because it plugs the very opening in the segment that it creates, causing rupturing of cells. To avoid these problems, the technician must perform extra steps when removing the segment from the prong. Also, the use of the above-described device requires the use of a test tube, which adds to the cost of the procedure.

Another known device provides a piercing needle inside a plastic sheath. The device is similar in configuration to the well-known needle assembly which is used to pierce and fill the typical blood collection tube. The device is located inside a test tube and its sharp cannula punctures the segment, after which blood passes through the cannula, out of the sheath, and into the test tube in which it is located. A major disadvantage of this device is that it also requires a test tube, which increases the cost of the procedure.

In both of the devices described above, a pipette is required to transfer droplets of diluted specimens from a first test tube, into other test tubes where tests are performed, thus increasing the cost and complexity of the procedure.

The present invention provides a device and method which overcome the disadvantages of the prior art described above.

SUMMARY OF THE INVENTION

The present invention comprises a container having a sharp cannula safely located inside the container. The container has interior walls which provide means for guiding a tube segment accurately onto the tip of the cannula, so that the cannula will reliably puncture the segment immediately upon insertion of the segment. The cannula allows the blood cells to pass unimpeded from the tube segment into the container. Blood cells leaving the tube segment are collected immediately in the container, which also provides a means to control the volume of cells collected. Also, one can add diluent to the blood specimen while it is in the container, after which the blood and the diluent are conveniently mixed either by shaking the device or agitating the contents by repeatedly squeezing the soft container. Moreover the container includes a spout which facilitates the transfer of accurately sized droplets of specimen.

The present invention therefore has the primary object of providing a device and method for removing a hazardous fluid from a sealed flexible tube.

The invention has the further object of providing a device and method as described above, wherein the fluid can be conveniently collected and diluted in the same container.

The invention has the further object of providing a device and method as described above, wherein the device has an integral spout which facilitates the dispensing of the fluid collected in the container.

The invention has the further object of providing a device and method which reliably prevents a hazardous fluid specimen from coming into contact with a person handling the specimen.

The invention has the further object of providing an accurate means for positioning a tube segment with respect to a piercing means, to achieve reliable puncturing.

The invention has the further object of forming a piercing means, a container, and a dispensing spout as a permanent assembly, having the combined function of piercing the tube segment, collecting fluid, and dispensing fluid.

The invention has the further object of dispensing a small, reproducible amount of a fluid specimen from a flexible tube.

The invention has the further object of reducing the number of test tubes and transfer pipettes required when typing and cross-matching samples of fluid between blood donors and recipients.

The reader will recognize other objects and advantages of the invention, from a reading of the following brief description of the drawings, the detailed description of the invention, and the appended claims.

DETAILED DESCRIPTION OF THE INVENTION

Figure 1:
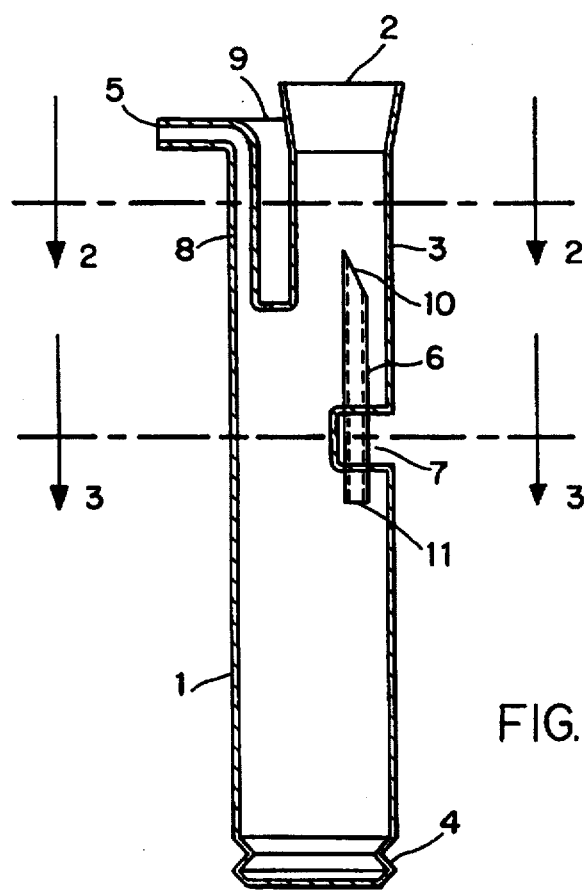
FIG. 1 is a cross-sectional elevational view of the apparatus of the present invention.

As shown in FIG. 1, the device of the present invention comprises a container having a body 1 and a neck portion 3, the neck portion having tapered opening 2. Spout 8, which is preferably (but not necessarily) integrally formed with body 1, has an exit nozzle 5 which may be dimensioned to produce drops of various sizes. The bottom of the device has an accordion shaped portion 4 which, as described below, serves as a trap for fluid.

Cannula 6 is housed and supported by support member 7. The cannula communicates through the support member, allowing fluid to pass from the sharp tip 10 to the exit 11. Typically the cannula is glued inside the support member, and is positioned near the central region defined by the opening. In the preferred embodiment, the support member is a dimple formed integrally with the wall of body 1, thereby providing maximum strength and requiring no additional parts. From the exterior of the container, the dimple defines a recess or indentation.

In the preferred embodiment, as shown in FIG. 1, the cannula is held at two distinct locations. The separation of these locations of attachment enhances the strength and stability with which the cannula is mounted to the container. The glue for affixing the cannula to the support member can be conveniently applied to the external side of the dimple, i.e. in the exterior recess, thereby sealing the regions where the dimple abuts the cannula.

Figure 2:
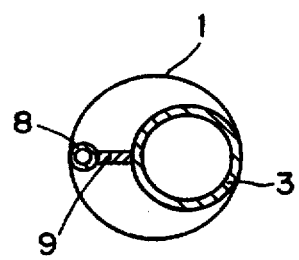
FIG. 2 is a cross-sectional view of the apparatus, taken along the lines 2—2 of FIG. 1.

FIG. 2 shows a cross-sectional view, taken along the line 2—2 of FIG. 1. FIG. 2 further illustrates the neck 3 and the spout 8. Neck 3 may also have an oval or square cross-section to conform more closely to the configuration of the tube segment containing the specimen. The member 9 provides a means to connect the spout to the neck to provide strength.

Figure 3:
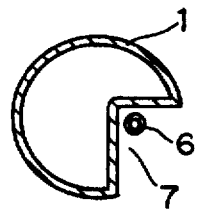
FIG. 3 is a cross-sectional view of the apparatus, taken along the lines 3—3 of FIG. 1.

FIG. 3 shows a cross-sectional view, taken along the line 3—3 of FIG. 1. FIG. 3 shows how the dimpled support member 7 is formed in the side of the body 1 with cannula 6 passing through.

Figure 11:
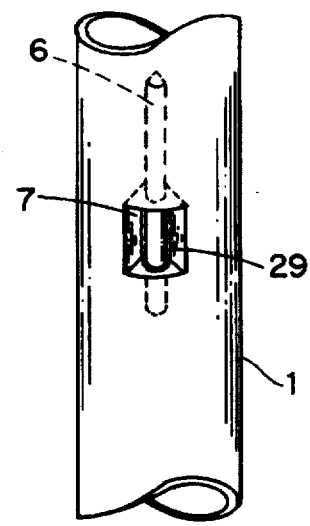
FIG. 11 provides a fragmentary perspective view showing the use of adhesive to seal the cannula from the outside.

FIG. 11 provides a fragmentary perspective view, showing the mounting of cannula 6 within dimpled support member 7. FIG. 11 shows adhesive material 29 which not only helps to anchor the cannula within the dimpled support member, but also seals the holes, formed in the dimple by the cannula, from the outside. Thus, no fluid will leak between the inside and the outside of the container.

The material used for the container is preferably polyethylene, or the like, which is relatively soft, so that the body can be squeezed. However, the invention is not limited to the use of a particular material. Though not a preferable alternative, the apparatus could be made of a rigid material and still enjoy some of the benefits of the disclosed structure.

Figure 4:
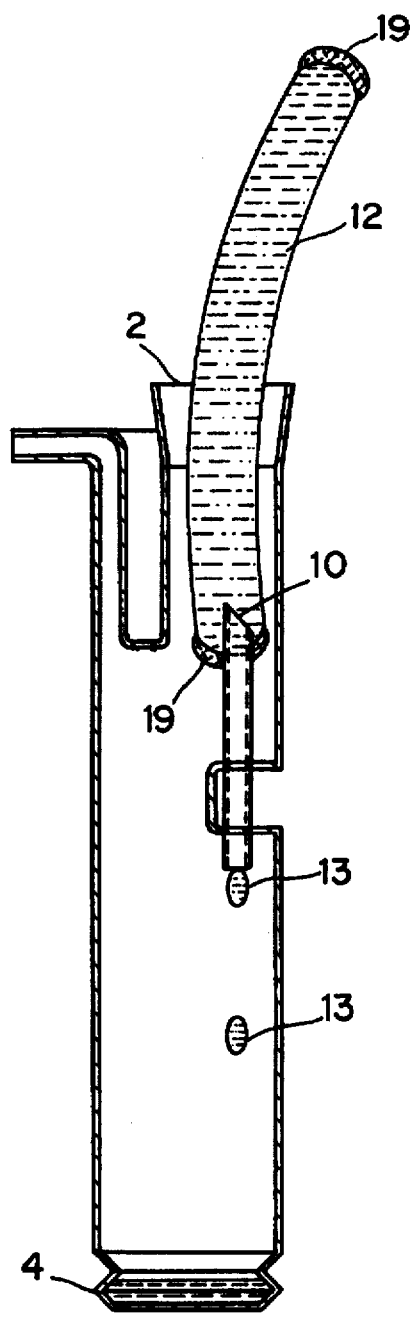
FIG. 4 provides a diagram showing the use of the apparatus of the present invention, wherein a sealed tubular segment is being inserted into the apparatus.

FIGS. 4-7 show the use of the apparatus of the present invention. As shown in FIG. 4, the method begins with tubular segment 12, which has pinched end 19, and which contains the blood or other fluid specimen to be sampled. The segment is inserted through the tapered opening 2 and down into the neck portion, until the sharp cannula tip 10 penetrates the segment. Then the segment is squeezed and its contained cells pass through the cannula, emerging as droplets 13 which are accumulated in a reservoir at the bottom 4. Subsequently the tube segment is removed.

Figure 5:
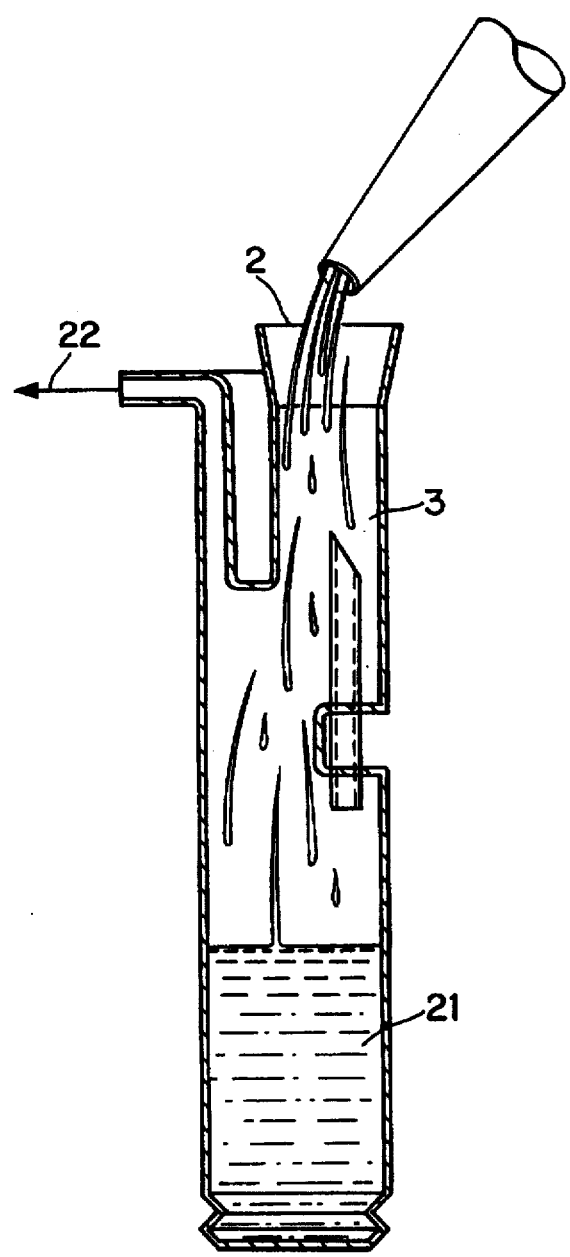
FIG. 5 provides another diagram showing the apparatus in use, wherein a diluent is being injected into the apparatus.

FIG. 5 shows the injection of diluent through tapered opening 2 and neck 3. When the diluent reaches the bottom, it mixes with the reservoir of cells, forming a mixture 21. The objects in the path of the incoming diluent, such as the dimple and the cannula, create turbulence which assists in the mixing. During the procedure, the spout vents air 22 from the body as the diluent is added, avoiding clogging of diluent due to surface tension in the small confines of neck 3. For further mixing of the diluent with the cells, the body is squeezed repeatedly.

Figure 6:
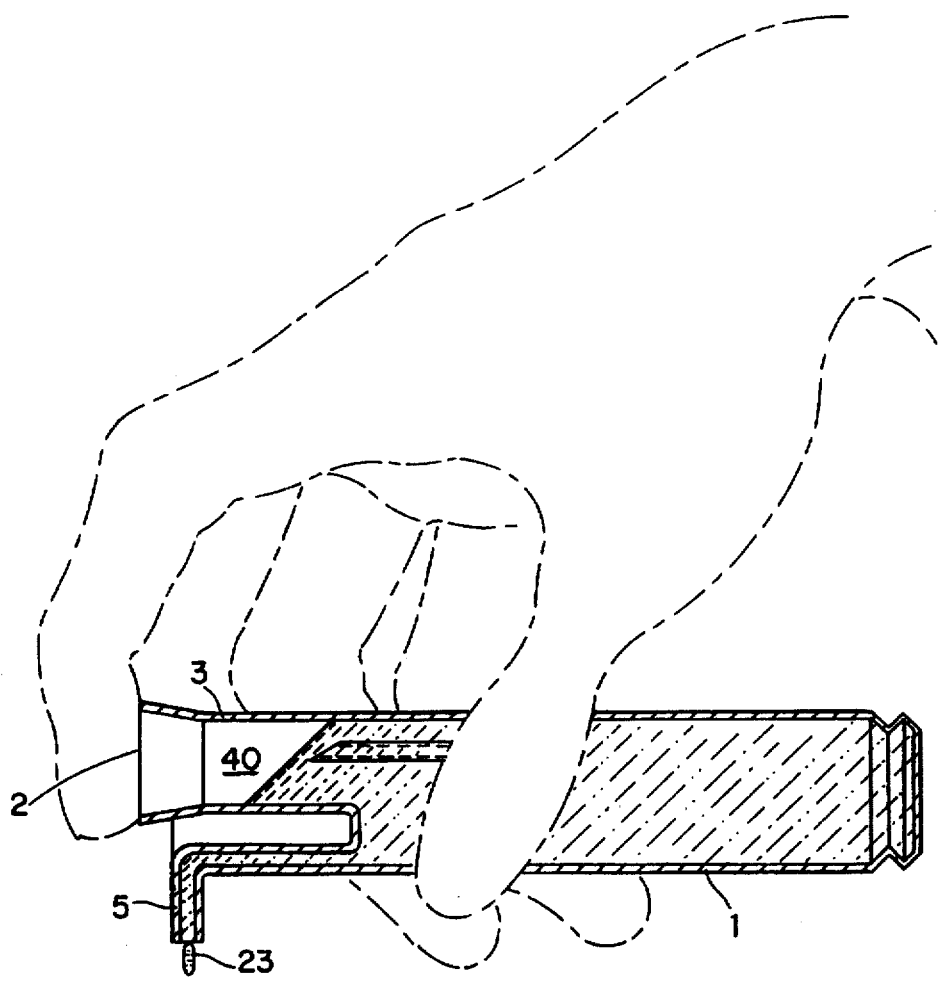
FIG. 6 provides another diagram showing the apparatus in use, wherein fluid is being dispensed from the apparatus.
Figure 6:
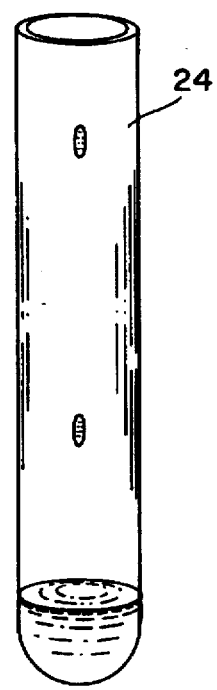

FIG. 6 shows the dispensing of droplets of liquid from the spout of the apparatus of the present invention. To dispense the liquid specimen, one first covers and seals the tapered opening 2 with the index finger, as shown. Then, after rotating the device to a generally horizontal position, one squeezes body 1, causing a droplet 23 to exit, typically into a test tube 24. The finger ensures that no liquid exits from the neck portion 3, and also prevents air from entering the device so that the rate of flow of droplets can be controlled entirely by squeezing. The diameter of the tip 5 of the spout controls the size of the droplet, as is well-known from the field of fluid nozzles. Also, an air lock 40 is created in the sealed neck, thus preventing specimen from reaching and contaminating the finger.

Figure 7:
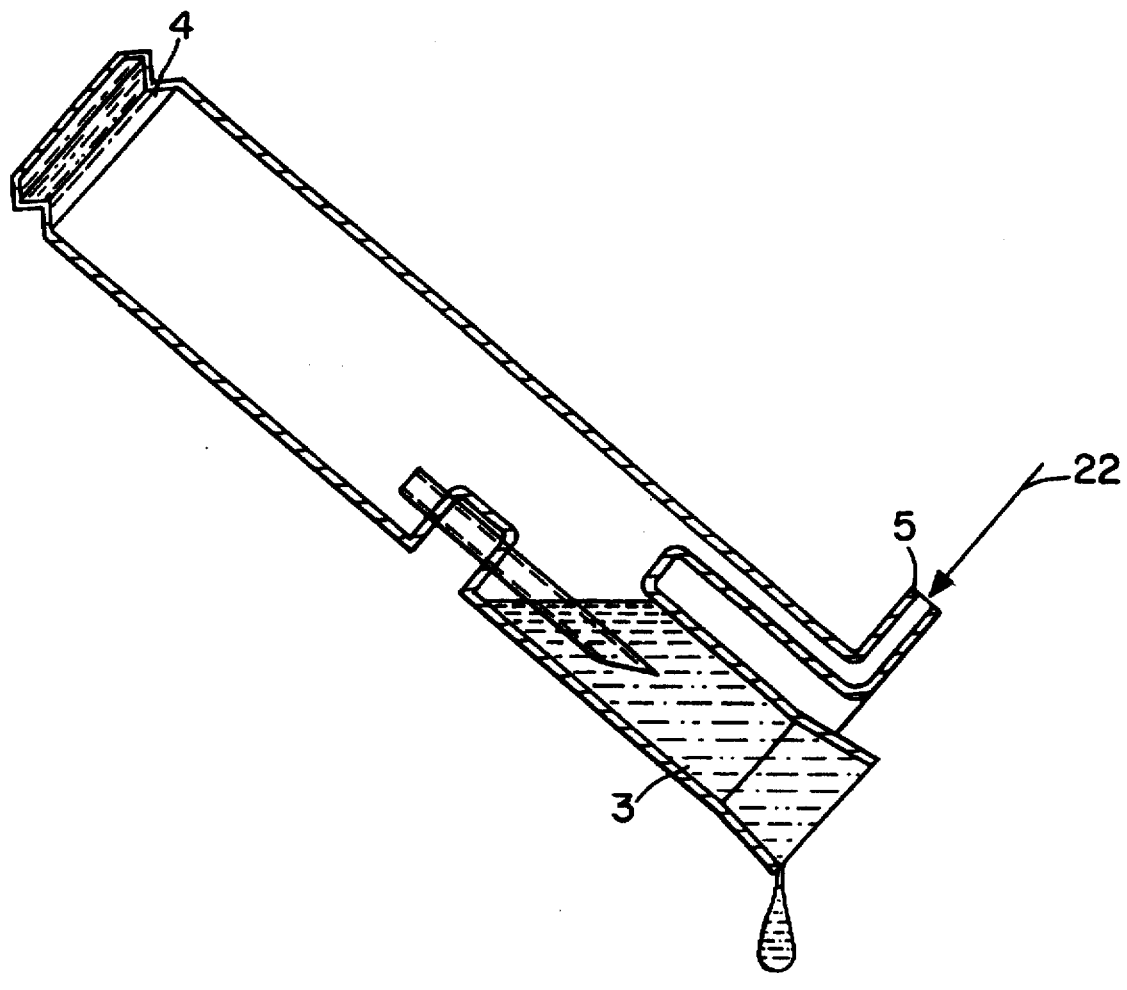
FIG. 7 provides another diagram showing the apparatus in use, wherein the diluent in the apparatus is decanted to separate it from the heavier material collected at the bottom of the apparatus.

As shown in FIG. 7, the device of the present invention can be used to decant, when it is desired to remove the diluent from the cells. Prior to the decanting step, it is assumed that the device has been subjected to centrifugation, which forces the heavier cells to the bottom 4 while the lighter diluent rests on top. When the device is turned upside down as shown in FIG. 7, the diluent pours through the neck 3 while air 22 is vented through spout 5. It is necessary to orient the device so the spout is above the neck. In this way the spout is prevented from becoming clogged with fluid, thus maintaining its venting function, and all the unwanted fluid pours readily out the neck.

The accordion-like shape of the bottom portion 4 of the device tends to prevent the cells at the bottom from pouring out. The accordion shape maximizes the effect of surface tension, which is known to trap fluids in tight chambers.

Figure 9:
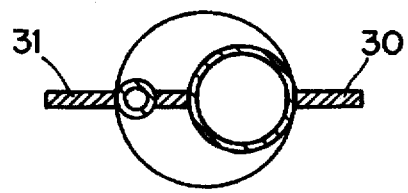
FIG. 9 is a cross-sectional view of the alternate embodiment, taken along the lines 9—9 of FIG. 8.
Figure 8:
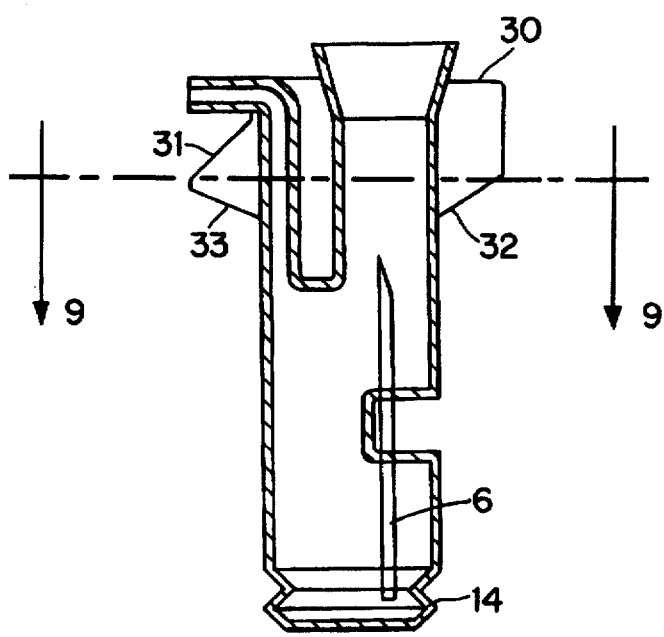
FIG. 8 is an elevational view of an alternative embodiment of the present invention.
Figure 10:
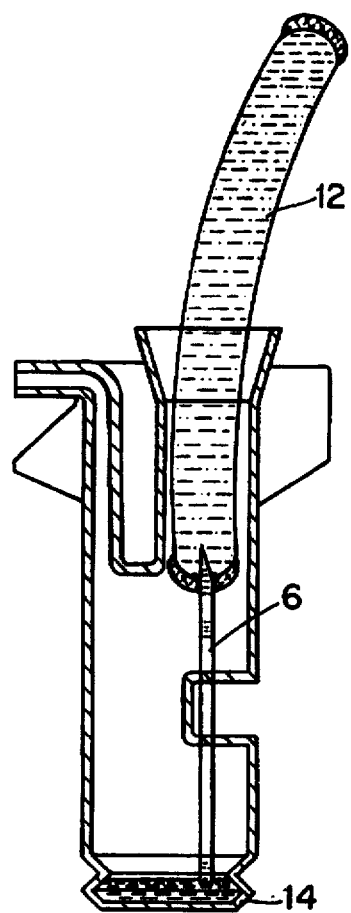
FIG. 10 provides a diagram showing the alternate embodiment in use, wherein a tubular segment is being inserted into the apparatus.

FIGS. 8–10 show an alternate embodiment in which cannula 6 is extended so that its end resides in the well 14 at the bottom of the body. The gap between the end of the cannula and the bottom of the container determines the volume of cells retained, as will be described below. To reduce the length of the cannula, one can make this embodiment shorter than that of FIG. 1. But the shortened length requires supporting members 30 and 31 which permit the device to hang from the circular openings in racks and centrifuges (not shown) since the length may be too short to be supported at its bottom in existing racks and centrifuges. Also chamfers 32 and 33 serve to centralize the devices in the circular openings.

FIG. 9 is a cross-sectional view taken along the line 9—9 of FIG. 8, and further shows how the members 30 and 31 are configured.

FIG. 10 shows the alternate embodiment in use. With the segment 12 inserted into the neck and punctured by the cannula 6, the cells which pass through the cannula upon squeezing the segment are deposited directly in well 14 when the segment is squeezed. However, when squeezing is relaxed, the segment sucks back a portion of the cells from well 14, through the cannula, returning them to the tube segment. The cells which remain at the bottom are kept there by the surface tension due to the configuration of the well. Thus a generally predictable volume of cells is retained in the well, which improves the consistency of the specimen sampling procedure. The volume can be affected by varying the height of the end of the cannula above the bottom of the well.

In the embodiment of FIGS. 8–10, the body is shorter because with better control of the volume of cells, the amount of diluent can be reduced and therefore the body requires a smaller volume. Thus, this embodiment reduces the cost of the material. However, the shorter body needs to be supported in racks and centrifuges which are designed for longer devices. Supports 30 and 31 are included for this purpose. Chamfers 32 and 33 provide means to centralize the device when it is being supported.

While the invention has been described with respect to specific embodiments, the person skilled in the art will recognize that many variations are possible. Such variations should be considered within the spirit and scope of the following claims.

What is claimed is:

1. Apparatus for removing a fluid specimen from a flexible tube, the apparatus comprising:
    a) a container having an opening sized for receiving the flexible tube which holds the specimen,
    b) a cannula having a sharp end, the cannula being located entirely inside the container and being affixed to the container, the cannula being positioned such that the sharp end will pierce the tube when the tube is inserted into the opening, and
    c) spout means connected to the container and defining a path for fluid flow, said path being distinct from said opening,
    wherein the container includes a permanently closed-off bottom portion opposite the opening, the bottom portion having a reduced-diameter part which comprises means for retaining some of said specimen by surface tension.

2. The apparatus of claim 1, wherein the opening includes a tapered portion.

3. The apparatus of claim 1, wherein the cannula is supported by a dimple which is integral with the container, wherein the cannula extends through at least a portion of the dimple.

4. The apparatus of claim 3, wherein the cannula extends through two distinct layers of material defining the dimple.

5. The apparatus of claim 3, wherein the dimple defines an indentation in an exterior surface of the container, and wherein at least a portion of the indentation is filled with an adhesive material.

6. The apparatus of claim 1, wherein the opening has a central region, and wherein the cannula is held in a position which is near the central region.

7. The apparatus of claim 1, wherein the opening is formed in a neck portion, and wherein the apparatus further comprises a member which connects the spout means to the neck portion.

8. The apparatus of claim 1, wherein the container has a bottom, and wherein the cannula extends substantially to the bottom of the container.

9. The apparatus of claim 1, wherein the container is made of a flexible material.

10. The apparatus of claim 1, wherein the container has a bottom, and wherein the cannula does not extend to the bottom of the container.

11. The apparatus of claim 1, wherein the apparatus includes a support means for suspending the apparatus from a rack.

12. The apparatus of claim 11, wherein the support means includes a chamfer for centralizing the apparatus in a rack.

13. Apparatus for removing a fluid specimen from a flexible tube, the apparatus comprising:
    a) a container having an opening sized for receiving the flexible tube which holds the specimen,
    b) a cannula having a sharp end, the cannula being located entirely inside the container and being affixed to the container, the cannula being positioned such that the sharp end will pierce the tube when the tube is inserted into the opening, and
    c) spout means connected to the container and defining a path for fluid flow, said path being distinct from said opening,
    wherein the cannula is supported by a dimple which is integral with the container, wherein the cannula extends through at least a portion of the dimple, and
    wherein the cannula extends through two distinct layers of material defining the dimple.

14. Apparatus for removing fluid from a flexible tube, the apparatus comprising:
    a) a container having a wall and an opening, the container defining an interior region and an exterior region, and
    b) a cannula affixed to the wall of the container and positioned entirely within the interior region near the opening,
    wherein the wall of the container is formed with a dimple extending into the interior region, and wherein the cannula is inserted through at least a portion of the dimple, and
    wherein the container includes a permanently closed-off bottom portion opposite the opening, the bottom portion having a reduced-diameter part which comprises means for retaining some of said specimen by surface tension.

15. The apparatus of claim 14, wherein the cannula extends through two layers of material defining the dimple.

16. The apparatus of claim 14, wherein a portion of the cannula is exposed to the exterior region, and wherein the cannula is affixed to the dimple with an adhesive which also comprises means for sealing the dimple from the exterior region.

17. The apparatus of claim 14, wherein the cannula defines a channel for fluid flow, wherein the channel does not communicate with the exterior region.

18. In a container for collecting and dispensing fluid, the container having a generally cylindrical body portion, the improvement wherein the container has a closed bottom portion, the bottom portion being formed with an accordion-shaped structure,
   wherein the container has an opening and a spout, the spout being distinct from the opening, and wherein there is a cannula affixed to the container, the cannula being held entirely inside the container and being oriented such that a flexible tube inserted into the opening will become pierced by the cannula.

19. The improvement of claim 18, wherein the cannula is supported by a dimple which is integral with the container, the dimple extending into the container, the cannula extending through the dimple, the cannula being sealed to the dimple by an adhesive material.

20. Apparatus for removing a fluid specimen from a flexible tube, the apparatus comprising:
   a) a container having an opening sized for receiving the flexible tube which holds the specimen,
   b) a cannula having a sharp end, the cannula being located entirely inside the container and being affixed to the container, the cannula being positioned such that the sharp end will pierce the tube when the tube is inserted into the opening, and
   c) spout means connected to the container and defining a path for fluid flow, said path being distinct from said opening,
   wherein the cannula is supported by a dimple which is integral with the container, wherein the cannula extends through at least a portion of the dimple, and
   wherein the dimple defines an indentation in an exterior surface of the container, and wherein at least a portion of the indentation is filled with an adhesive material.

21. A method of removing, diluting, and dispensing fluid stored in a flexible tube, the method comprising the steps of:
   a) guiding the flexible tube into a container, the container having a sharp cannula disposed therein, the container having a bottom, the cannula having an opening spaced from the bottom, the guiding step being performed by pushing the tube through an opening in the container such that the tube becomes pierced by the cannula, and such that fluid flows out of the tube and collects at the bottom of the container,
   b) injecting a diluent through the opening, and
   c) dispensing diluted fluid from the container through a spout formed in the container, the spout being distinct from the opening,
   wherein the guiding step is followed by the step of squeezing the tube so as to dispense fluid from the tube, and into the cannula, and
   wherein the cannula extends substantially to the bottom of the container, and wherein the squeezing step is followed by the step of relaxing pressure on the tube so as to suck fluid back into the tube, so as to maintain a desired amount of fluid in the container.

22. The method of claim 21, further comprising the step of maintaining the spout in an open condition to permit venting of air in the container, while the injecting step is performed.

23. The method of claim 21, wherein the container is flexible, and wherein the injecting step is followed by the step of mixing fluid with the diluent by repeatedly squeezing the container.

24. The method of claim 21, wherein the dispensing step is performed by covering the opening so as to create an air lock, tilting the container, and squeezing the container.

25. The method of claim 21, wherein the spout has an exit tip, and wherein the method further comprises the step of determining a size of the exit tip according to a desired droplet size.

26. The method of claim 21, further comprising the step of decanting fluid from the container by tilting the container, while maintaining the spout in a higher position than that of the opening, such that fluid flows out of the opening, while venting air in the container through the spout.

27. A method of removing, diluting, and dispensing fluid stored in a flexible tube, the method comprising the steps of:
   a) guiding the flexible tube into a container, the container having a sharp cannula disposed therein, the container having a bottom, the cannula having an opening spaced from the bottom, the guiding step being performed by pushing the tube through an opening in the container such that the tube becomes pierced by the cannula, and such that fluid flows out of the tube and collects at the bottom of the container,
   b) injecting a diluent through the opening, and
   c) dispensing diluted fluid from the container through a spout formed in the container, the spout being distinct from the opening,
   wherein the container is flexible, and wherein the injecting step is followed by the step of mixing fluid with the diluent by repeatedly squeezing the container.

28. A method of removing, diluting, and dispensing fluid stored in a flexible tube, the method comprising the steps of:
   a) guiding the flexible tube into a container, the container having a sharp cannula disposed therein, the container having a bottom, the cannula having an opening spaced from the bottom, the guiding step being performed by pushing the tube through an opening in the container such that the tube becomes pierced by the cannula, and such that fluid flows out of the tube and collects at the bottom of the container,
   b) injecting a diluent through the opening, and
   c) dispensing diluted fluid from the container through a spout formed in the container, the spout being distinct from the opening,
   wherein the dispensing step is performed by covering the opening so as to create an air lock, tilting the container, and squeezing the container.

29. A method of removing, diluting, and dispensing fluid stored in a flexible tube, the method comprising the steps of:
   a) guiding the flexible tube into a container, the container having a sharp cannula disposed therein, the container having a bottom, the cannula having an opening spaced from the bottom, the guiding step being performed by pushing the tube through an opening in the container such that the tube becomes pierced by the cannula, and such that fluid flows out of the tube and collects at the bottom of the container,
   b) injecting a diluent through the opening, and c) dispensing diluted fluid from the container through a spout formed in the container, the spout being distinct from the opening, wherein the spout has an exit tip, and wherein the method further comprises the step of determining a size of the exit tip according to a desired droplet size.

30. A method of removing, diluting, and dispensing fluid stored in a flexible tube, the method comprising the steps of:

a) guiding the flexible tube into a container, the container having a sharp cannula disposed therein, the container having a bottom, the cannula having an opening spaced from the bottom, the guiding step being performed by pushing the tube through an opening in the container such that the tube becomes pierced by the cannula, and such that fluid flows out of the tube and collects at the bottom of the container, b) injecting a diluent through the opening, and c) dispensing diluted fluid from the container through a spout formed in the container, the spout being distinct from the opening, further comprising the step of decanting fluid from the container by tilting the container, while maintaining the spout in a higher position than that of the opening, such that fluid flows out of the opening, while venting air in the container through the spout.

31. Apparatus for removing a fluid specimen from a flexible tube, the apparatus comprising:

a) a container having an opening sized for receiving the flexible tube which holds the specimen, b) a cannula having a sharp end, the cannula being located entirely inside the container and being affixed to the container, the cannula being positioned such that the sharp end will pierce the tube when the tube is inserted into the opening, and c) spout means connected to the container and defining a path for fluid flow, said path being distinct from said opening, wherein the apparatus includes a support means for suspending the apparatus from a rack, and wherein the support means includes a chamfer for centralizing the apparatus in a rack.

32. Apparatus for removing fluid from a flexible tube, the apparatus comprising:

a) a container having a wall and an opening, the container defining an interior region and an exterior region, and b) a cannula affixed to the wall of the container and positioned entirely within the interior region near the opening, wherein the wall of the container is formed with a dimple extending into the interior region, and wherein the cannula is inserted through at least a portion of the dimple, wherein the cannula extends through two layers of material defining the dimple.

33. Apparatus for removing fluid from a flexible tube, the apparatus comprising:

a) a container having a wall and an opening, the container defining an interior region and an exterior region, and b) a cannula affixed to the wall of the container and positioned entirely within the interior region near the opening, wherein the wall of the container is formed with a dimple extending into the interior region, and wherein the cannula is inserted through at least a portion of the dimple, wherein a portion of the cannula is exposed to the exterior region, and wherein the cannula is affixed to the dimple with an adhesive which also comprises means for sealing the dimple from the exterior region.

34. In a container for collecting and dispensing fluid, the container having a generally cylindrical body portion, the improvement wherein the container has a closed bottom portion, the bottom portion being formed with an accordion-shaped structure, wherein the container has an opening and a spout, the spout being distinct from the opening, and wherein there is a cannula affixed to the container, the cannula being held entirely inside the container and being oriented such that a flexible tube inserted into the opening will become pierced by the cannula.

35. A method of removing, diluting, and dispensing fluid stored in a flexible tube, the method comprising the steps of:

a) guiding the flexible tube into a container, the container having a sharp cannula disposed therein, the container having a bottom, the cannula having an opening spaced from the bottom, the guiding step being performed by pushing the tube through an opening in the container such that the tube becomes pierced by the cannula, and such that fluid flows out of the tube and collects at the bottom of the container, b) injecting a diluent through the opening, and c) dispensing diluted fluid from the container through a spout formed in the container, the spout being distinct from the opening, wherein the guiding step is followed by the step of squeezing the tube so as to dispense fluid from the tube, and into the cannula, and wherein the cannula extends substantially to the bottom of the container, and wherein the squeezing step is followed by the step of relaxing pressure on the tube so as to suck fluid back into the tube, so as to maintain a desired amount of fluid in the container.

* * * * *